United States Patent
Kim et al.

(10) Patent No.: US 6,812,212 B2
(45) Date of Patent: Nov. 2, 2004

(54) ASSESSMENT OF OXIDANT STRESS IN VITRO AND IN VIVO

(76) Inventors: Hyesook Kim, 4683 Ravine Dr., Bloomfield Hills, MI (US) 48301; Elizabeth Starr Roberts-Kirchhoff, 35716 Main St., New Baltimore, MI (US) 78047

(*) Notice: Subject to any disclaimer, the term of this patent is extended or adjusted under 35 U.S.C. 154(b) by 38 days.

(21) Appl. No.: 09/915,776

(22) Filed: Jul. 26, 2001

(65) Prior Publication Data

US 2002/0022244 A1 Feb. 21, 2002

Related U.S. Application Data

(60) Provisional application No. 60/221,631, filed on Jul. 28, 2000.

(51) Int. Cl.[7] ............................................. A61K 38/00

(52) U.S. Cl. ...................................................... 514/18

(58) Field of Search ....................... 436/86, 89; 514/18

(56) References Cited

U.S. PATENT DOCUMENTS 4,029,768 A * 6/1977 Penn ......................... 424/570
6,133,039 A * 10/2000 Heinecke ..................... 436/89

OTHER PUBLICATIONS

Czech et al. J Invest Dermatol. Jan. 1997: 108–12.*
Gadelha et al. Arch Biochem Biophys. Sep. 1997 15:345(2):243–50.*
Brown GC, Borutaite V. Nitric oxide, cytochrome c and mitochondria. Biochem Soc Symp. 1999;66:17–25. (Abstact).*
Cassina AM, Hodara R, Souza JM, Thomson L, Castro L, Ischiropoulos H, Freeman BA, Radi R. Cytochrome c nitration by peroxynitrite. J Biol Chem. Jul. 14, 2000;275(28):21409–15.*
Ahern H. The Scientist, 1995, vol. 9, No.: 15, p. 20.*
Smith, W.L. Marnett, L.J. Biochim. Biophys. Acta, 1083: 1–17 (1991).
Baker, R.R. Clin. Biochem., 23: 455–458 (1990).
Smith, W.L. Biochem. J., 259: 315–324 (1989).
Lote, C.J. Haylor, J. Prostags. Leukos. Essen. Fatty Acids, 36: 203–217 (1989).
Xei, W., Robertson, D.L. and Simmons, D.L. Drug. Develop. Res. 25: 249–265 (1992).
Kujubu, D., Fletcher, B., Varnum, B., Lim, R., & Hershman, H.R. J. Biol. Chem. 266:12866–12872 (1991).
Smith, W. L. and DeWitt, D. L. Advances in Immunol. 62: 167–215 (1996).
White, S. Prostagland. Leuk. Essent. Fatty, 43: 209–222 (1991).

Miller, M. J. S., Thompson, J. H., Zhang, X–J., Sadowskakrowicka, H., Kakkis, J. L., Munshi, U. K., Sandoval, M., Rossi, J. L., Elobychilress, S., Beckman, J. S., Ye, Y. Z., Rodi, C. P., Manning, P. T., Currie, M. G., and Clark, D. A. (1995) Gastroenterology 109, 1475–1483.

Reuter, B. K., Asfaha, S., Buret, A., Sharkey, K. A., and Wallace, J. L. (1996) J. Clin. Invest., 98, 2076–2085.

Singer, I. I., Kawka, D. W., Scott, S., Weinder, J. R., Mumford, R. A., Riehl, T. E., and Stenson, W. F. (1996) Gastroenterology 111, 871–885.

Green, D. R. and Reed, J. C. (1998) Science 281, 1309–1312 and references therein.

Gunther, M. R., Hsi, L. C., Curtis, J. F., Gierse, J. K., Marnett, L. J., Eiling, T. E., and Mason, R. P. (1997) J. Biol. Chem. 272, 17086–17090.

Rossig, L., Fichtlscherer, B., Breitschopf, K., Haendeler, J., Zeiher, A. M., Mulsch, A., and Dimmeler, S. (1999) J. Biol. Chem. 274,6828–6826.

Lepoivre, M., Fieschi, F., Coves, J., Thelander, L., Fontecave, M. (1991) Biochem. Biophys. Res. Commun. 179, 442–448.

Roberts, E. S., Lin, H–L., Crowley, J. R., Vuletich, J. L., Osawa, Y., and Hollenberg, P. F. (1998) Chem. Res. Toxicol. 11, 1067–1074.

Hajjar, D. P., Lander, H. M., Pearce, S. F. A., Upmacis, R. K., and Pomerantz, K. B. (1995) J. Am. Chem. Soc. 117, 3340–3346.

Laemmli, U. K. (1970) Nature, 277, 680–685.

Kim, H., Kim, S. G., Lee, M. Y., and Novak, R. F. (1992) Biochem. Biophys. Res. Commun. 186, 846–853.

Kim, H., Putt, D., Reddy, S., Hollenberg, P. F., and Novak, R. F. (1993) J. Pharmacol. Exp. Ther. 267, 927–936.

Hla, T., and Neilson, K., Proc. Natl. Acad. Sci. U.S.A. 89:7384–7388 (1992).

Ye, Y.Z., Strong, M., Huang, Z. and Beckman, J.S. (1996) *in* Methods in Enzymology (Packer, L. ed) vol. 269, pp. 201–209, Acedemic Press Inc., New York, N. Y.

* cited by examiner

Primary Examiner—Karen Cochrane Carlson
(74) Attorney, Agent, or Firm—Kohn & Associates, PLLC (57) ABSTRACT

There is provided a method of assessing oxidant stress by measuring polymerization of proteins. Also provided is a marker for oxidant stress which includes a polymerized protein. A kit for use in assessing oxidant stress, the kit including an assay for detecting polymerized proteins is also provided. A method of lowering oxidant stress by administering to a patient an effective amount of at least one reducing agent is also provided. A pharmaceutical composition for lowering oxidant stress, the pharmaceutical having an effective amount of reducing agent and a pharmaceutically acceptable carrier is also provided.

9 Claims, 8 Drawing Sheets

ASSESSMENT OF OXIDANT STRESS IN VITRO AND IN VIVO

CROSS-RELATED REFERENCE SECTION

This application claims the benefit of priority under 35 U.S.C. Section 119(e) of United States Provisional Patent Application No. 60/221,631, filed Jul. 28, 2000, which is incorporated herein by reference.

GOVERNMENT SUPPORT

Research in this application was supported in part by a contract from National Institute of Environmental Health Sciences (N43 ES 95438). The government has certain rights in the invention.

BACKGROUND OF INVENTION

1. Field of the Invention

The present invention generally relates to methods of assessing and preventing oxidant stress in vitro and in vivo. More specifically, the present invention relates to methods of measuring nitration and polymerization of proteins which can be used for assessing oxidant stress and methods of preventing nitration and/or polymerization of protein due to oxidant stress.

2. Description of Related Art

It is generally known in the art that superoxide is produced under oxidant stress. This reactive molecule directly or indirectly reacts with macromolecules such as DNAs and proteins and depletes reducing agents such as glutathione in the cells.

Prostaglandin $H_2$ synthases, which are membrane-bound enzymes, catalyze the committed step in the biosynthesis of the prostaglandins and thromboxanes. Prostaglandin $H_2$ synthases have cyclooxygenase and peroxidase activities (1). Prostaglandin $H_2$ synthases add molecular oxygen to arachidonic acid to form prostaglandin $G_2$. Prostaglandin $G_2$ is then rapidly converted to prostaglandin $H_2$ by reduction of the peroxide to a hydroxyl group. Prostaglandin $H_2$ is enzymatically or non-enzymatically converted to prostaglandin $F_2\alpha$, prostaglandin $E_2$, prostaglandin $D_2$, prostaglandin $I_2$ (prostacyclin) or thromboxane $A_2$ (2–4). In addition to constitutively expressed prostaglandin $H_2$ synthase form 1, a second inducible form of prostaglandin $H_2$ synthase, prostaglandin $H_2$ synthase form 2, was discovered in chicken fibroblasts (5) and murine 3T3 cells (6). Prostaglandin $H_2$ synthase form 2 is similar to prostaglandin $H_2$ synthase form 1 with regard to molecular size, subunit composition, and general reaction mechanism. The two prostaglandin $H_2$ synthase isoforms have 60% identity in their primary sequences (7).

Prostaglandin biosynthesis is the target for non-steroidal anti-inflammatory drugs (NSAIDs). Prostaglandin $H_2$ synthase is the primary target of aspirin, indomethacin, ibuprofen, and other NSAIDs (5,8). Increased expression of both inducible nitric oxide (NO) synthase and prostaglandin $H_2$ synthase form 2 has been reported in intestinal inflammation (9–11).

Cytochrome c induces apoptosis by translocation from the mitochondrial membrane to the cytoplasm followed by binding to the apoptotic protease activating factor-1 (Apaf-1) which activates caspases (12). Nitration and/or polymerization of cytochrome c in mitochondria may compromise its translocation and/or its caspase activation function.

Nitration of several amino acid residues of proteins is a result of the reaction of NO with superoxide which is produced under oxidant stress to form peroxynitrite, a potent toxic oxidant. Recently, it was reported that nitrotyrosine was also formed via a tyrosyl radical produced during catalysis of prostaglandin $H_2$ synthase form 2 (13). Nitration of caspase-3 (14), ribonucleotide reductase (15), and cytochrome P450 2B1 (16) resulted in loss of catalytic activity. Interestingly, nitration of cysteine residue of ovine prostaglandin $H_2$ synthase form 1 enhanced catalytic activity by alteration of secondary structure of the enzyme (17).

While it is well known in the art that oxidant stress can lead to further problems within the body which, as set forth above, there are no methods or products which limit or eliminate oxidant stress. These problems can include cancer and other ailments. Accordingly, it is desirable to develop new methods and markers for determining oxidant stress.

SUMMARY OF THE INVENTION

According to the present invention, there is provided a method of assessing oxidant stress by measuring polymerization of proteins. Also provided is a marker for oxidant stress which includes a polymerized protein. A kit for use in assessing oxidant stress, the kit including an assay for detecting polymerized proteins is also provided. A method of lowering oxidant stress by administering to a patient an effective amount of at least one reducing agent is also provided. A pharmaceutical composition for lowering oxidant stress, the pharmaceutical having an effective amount of reducing agent and a pharmaceutically acceptable carrier is also provided.

DESCRIPTION OF THE DRAWINGS

Other advantages of the present invention will be readily appreciated as the same becomes better understood by reference to the following detailed description when considered in connection with the accompanying drawings wherein:

FIG. 3 Panels A and B show the inhibition of nitration of prostaglandin $H_2$ synthase form 2 (PGHS-2) by addition of glutathione (GSH); nitration was induced by treatment of peroxynitrite (PN); lane 1 included 16 μg of sheep PGHS-2 without treatment; lanes 2 and 3 included PGHS-2 with 450 μM of PN and 31 μM of GSH treatment; and lanes 4 and 5 included PGHS-2 with PN treatment; samples were denatured with β-mercaptoethanol (β-ME) contained in the loading buffer were analyzed by SDS-PAGE; the proteins were electroblotted to a nitrocellulose membrane and Western blot analysis was carried out using monoclonal antibodies against nitrotyrosine with an alkaline phosphatase system;

FIGS. 5A and B, show dimerization of prostaglandin $H_2$ synthase form 2 (PGHS-2) via a cysteine disulfide-bond following treatment with peroxynitrite (PN). Lane 1 included 16 μg of sheep PGHS-2 without treatment; lanes 2 and 3 included PGHS-2 with 450 μM of PN and 31 μM of glutathione treatment; and lanes 4 and 5 included PGHS-2 with PN treatment; samples were analyzed by SDS-PAGE without β-mercaptoethanol in the loading buffer; proteins were electroblotted to a nitrocellulose membrane and Western blot analysis was carried out using either antibodies against nitrotyrosine (Panel A) or antibodies against PGHS-2 (Panels B-1 and B-2) with a horseradish peroxidase-ECL (Panel B-1) or alkaline phosphatase-ECL (Panel B-2) system; and FIGS. 6A and B, show prostaglandin $H_2$ synthase form 2 (PGHS-2) nitrated and dimerized in vivo; Panel A shows sheep PGHS-2 (16 μg) analyzed by SDS-PAGE with β-mercaptoethanol (+βME) in the loading buffer; Panel B shows PGHS-2 (16 μg) without treatment analyzed by SDS-PAGE without β-mercaptoethanol (−βME) in the loading buffer; the proteins were electroblotted to a nitrocellulose membrane and Western blot analysis was carried out using either antibodies against nitrotyrosine (Panel A and Panel B-3) or antibodies against PGHS-2 (Panel B-2), coomassie blue staining of the PGHS-2 after SDS-PAGE was carried out without this addition of β-ME (−βME) in the loading buffer is shown in Panel B-2.

DETAILED DESCRIPTION OF THE INVENTION

The present invention generally provides a method to assess oxidant stress by measuring polymerized proteins. The polymerized proteins can be assessed by conventional detection methods including electrophoresis, chromatography, or Western blot analysis using antibody against the protein or nitrated amino acid residues.

The present invention also provides a method to assess oxidant stress by measuring nitrated and polymerized proteins. The nitrated and polymerized proteins can be separated by conventional methods including electrophoresis and chromatography and detected by Western blot analysis using antibodies against nitrated amino acid residues. The method further includes assessing oxidant stress by measuring formation of protein polymers connected by disulfide bonds. The methods of the present invention include methods to assess oxidant stress by measuring polymerized cytochrome c and prostaglandin $H_2$ synthases induced by oxidants such as peroxynitrite, a potent toxic oxidant. Peroxynitrite is formed as a result of reaction of NO with superoxide produced under oxidant stress.

The method includes assessing oxidant stress by measuring cytochrome c nitrated by oxidants such as peroxynitrite.

Oxidant stress in biological systems disrupts cellular structures and functions, and contributes to disease development. By assessing oxidant stress, it is meant that the present inventive assay is capable of being an indication of oxidant stress in vitro and in vivo. In combination with conventional detection methods, the assay indicates a relationship between oxidant stress and proteins nitrated and/or polymerized via disulfide or non-disulfide bonds.

Previously no studies have been reported on oxidant stress-induced polymerization and especially simultaneous nitration and polymerization of a protein. Moreover polymerization of proteins by oxidant stress via sulfur hydryl group of cysteine residues and prevention of the polymerization by addition of a reducing agent has not been reported. Existence of the disulfide boned dimeric form of prostaglandin $H_2$ synthases is therefore unexpected.

Figure 1A:
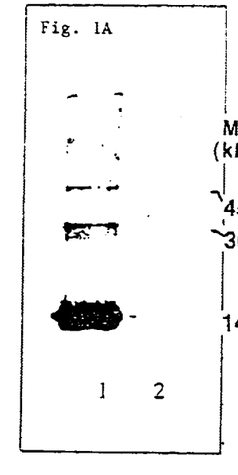
FIGS. 1A–C shows the concentration-dependent nitration of cytochrome c by peroxynitrite (PN); Panel A, in lanes 1 and 2, shows SDS-PAGE analysis of 2 μg of cytochrome c obtained after incubation with 0.5 mM PN and deactivated PN, respectively; Panel B shows that cytochrome c was incubated with various concentrations of PN (0.032 to 0.13 mM); each lane contains 0.5 μg of cytochrome c; Panel C shows analysis of Western blot analysis shown in FIG. 1, Panel B and blots from two other experiments; bands were quantitated using a Molecular Dynamics Personal Densitometer; Western blot analysis was carried out with polyclonal antibodies produced against nitrotyrosine using the alkaline phosphatases system.
Figure 1B:
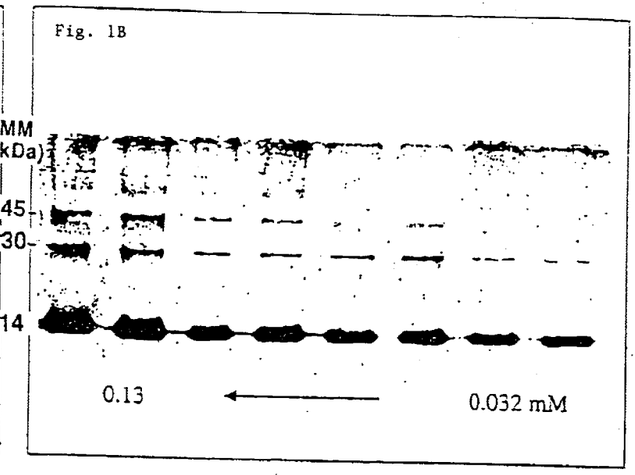
Figure 1C:
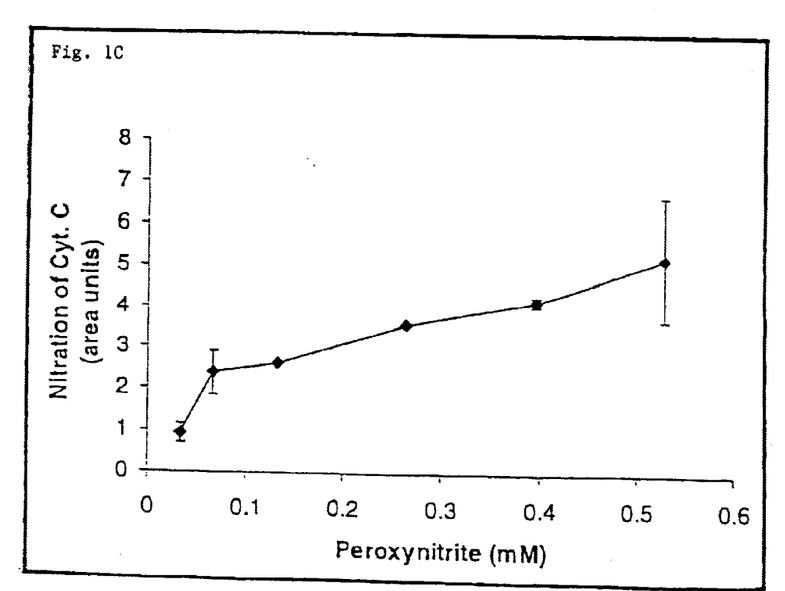
Figure 1D:
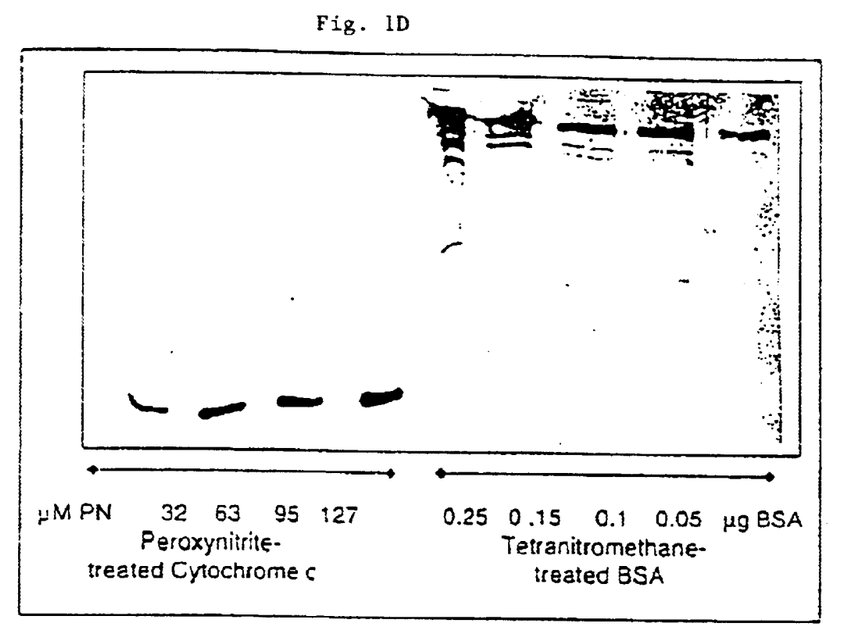
FIGS. 1D and E show quantitation of nitrotyrosine in peroxynitrite-treated cytochrome c; Panel D shows Western blot analysis of peroxynitrite-treated cytochrome c and tetranitromethane-treated bovine serum albumin (BSA); Panel E shows the amount of nitrotyrosine per pmol of cytochrome c at each of the peroxynitrite concentrations; quantitation of cytochrome c content in peroxynitrite-treated cytochrome c was determined with nitrated BSA as standard.
Figure 1E:
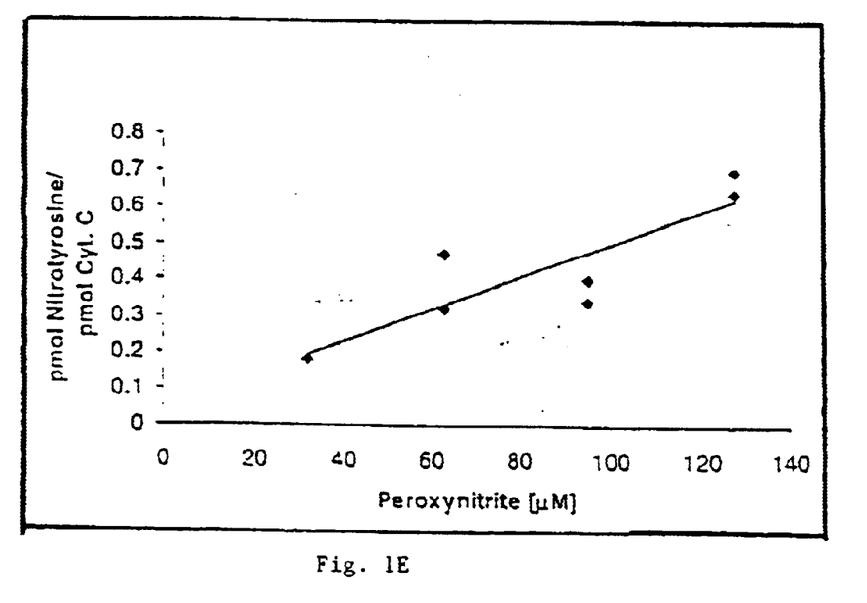
Figure 2:
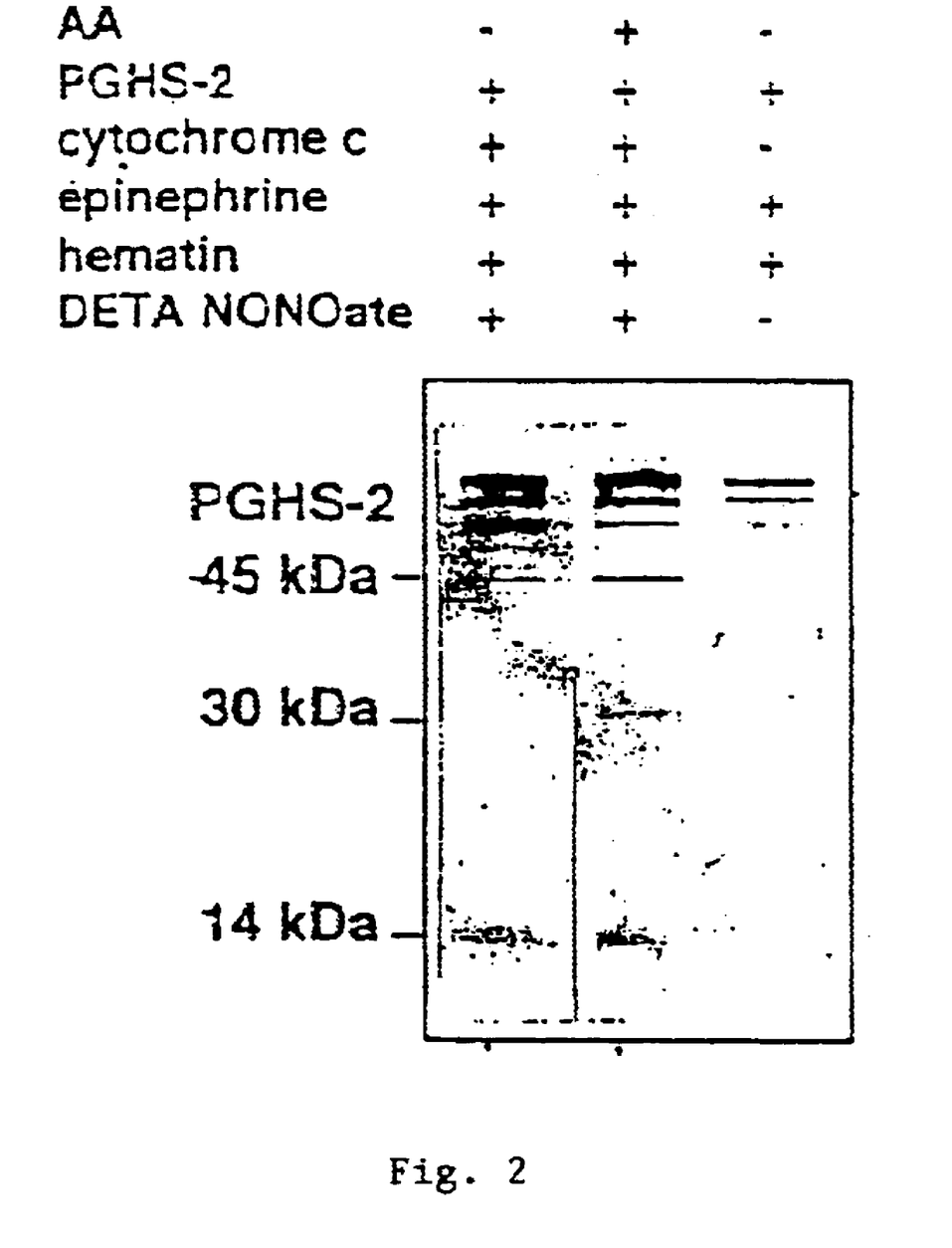
FIG. 2 shows the effect of arachidonic acid (AA) metabolism of prostaglandin $H_2$ synthase form 2 (PGHS-2) on nitration of cytochrome c, the reaction mixture contained cytochrome c, 40 μg, ovine PGHS-2, 104 units, AA, 590 μM, epinephrine, 31 μg, hematin, 1 μM, and diethylenetetraamine (DETA) NONOate (NO donor), 300 μM, as indicated in the figure; the reaction mixture in 100 mM phosphate buffer with a pH of 7.4 (total volume, 200 μl) was incubated at 37° C. for 30 minutes; each lane contained 8 μl of reaction mixture; proteins were separated by SDS-PAGE. Western blot analysis was carried out with monoclonal antibodies produced against nitrotyrosine using the alkaline phosphatase system.

Polymerization of cytochrome c after peroxynitrite treatment occurs via non-disulfide bonds. Nitration and polymerization of cytochrome c after peroxynitrite treatment is dose-dependent (FIG. 1). Cytochrome c was nitrated and polymerized when peroxynitrite was replaced with NO donor (DETA NONOate) in the presence of peroxide produced by prostaglandin $H_2$ synthase during catalysis of arachidonic acid (FIG. 2). Existence of a nitrated species with a molecular mass of 30 or 45 kDa species was indicative of oxidant stress.

Figure 6:
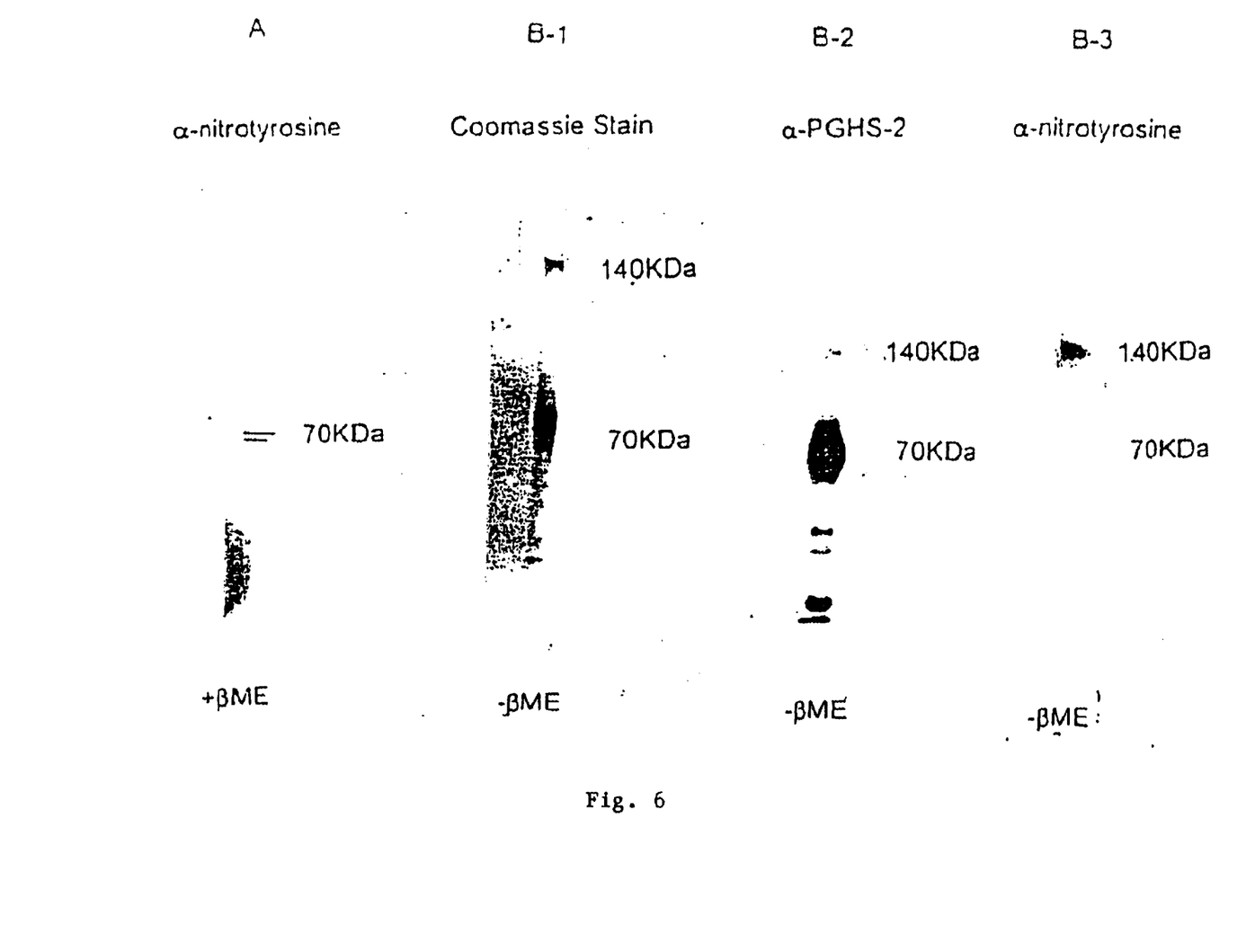

Prostaglandin $H_2$ synthase form 2, isolated from sheep placenta, contained nitrated tyrosine residues (FIGS. 2 and 6). The native prostaglandin $H_2$ synthase form 2 was found to be dimerized via a cysteine-disulfide bond. The prostaglandin $H_2$ synthase form 2 dimer contained higher levels of nitrated tyrosine residues compared with the monomer (FIG. 6). The in vivo nitration and dimerization of prostaglandin $H_2$ synthase form 2 was a result of oxidant stress mediated by prostaglandin $H_2$ synthase and NO synthase. Nitration and polymerization of prostaglandin $H_2$ synthase was not an artifact which occurred during purification of the enzyme considering this extremely unstable enzyme maintained its activity.

Dimerization of prostaglandin $H_2$ synthase via cysteine disulfide bond also occurred in vitro. Prostaglandin $H_2$ synthase was dimerized via cysteine-disulfide bond after peroxynitrite treatment and the prostaglandin $H_2$ synthase dimer contained higher levels of nitrated tyrosine residues compared with the monomer (FIG. 6).

In the previously reported experiments, prostaglandin $H_2$ synthase was treated with β-mercaptoethanol to break disulfide bonds prior to separation of the prostaglandin $H_2$ synthase by electrophoresis. Breakage of disulfide bonds by addition of β-mercaptoethanol prevented researchers determining that prostaglandin synthase was polymerized by disulfide bonds by oxidant insults in vitro or in vivo.

Figure 3A:
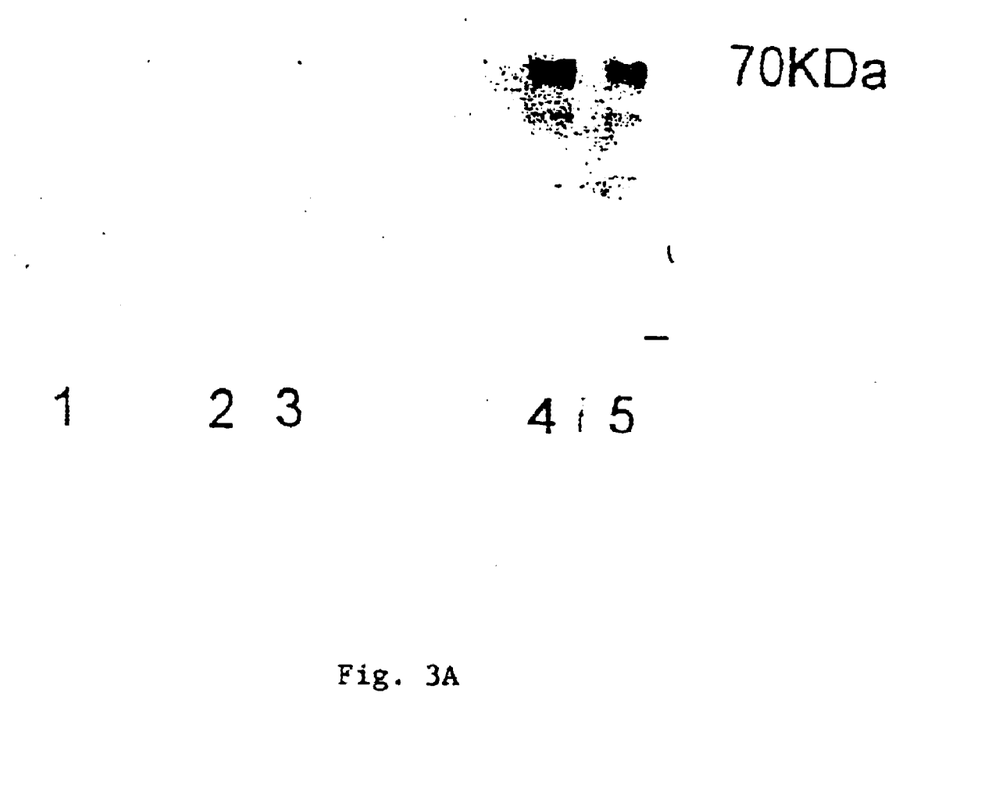
Figure 3B:
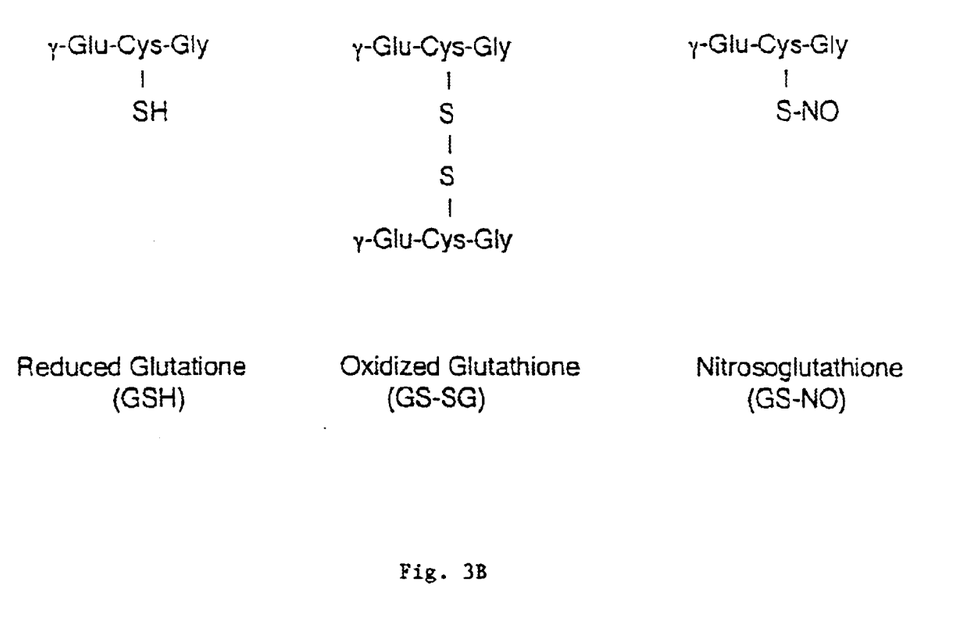
Figure 5:
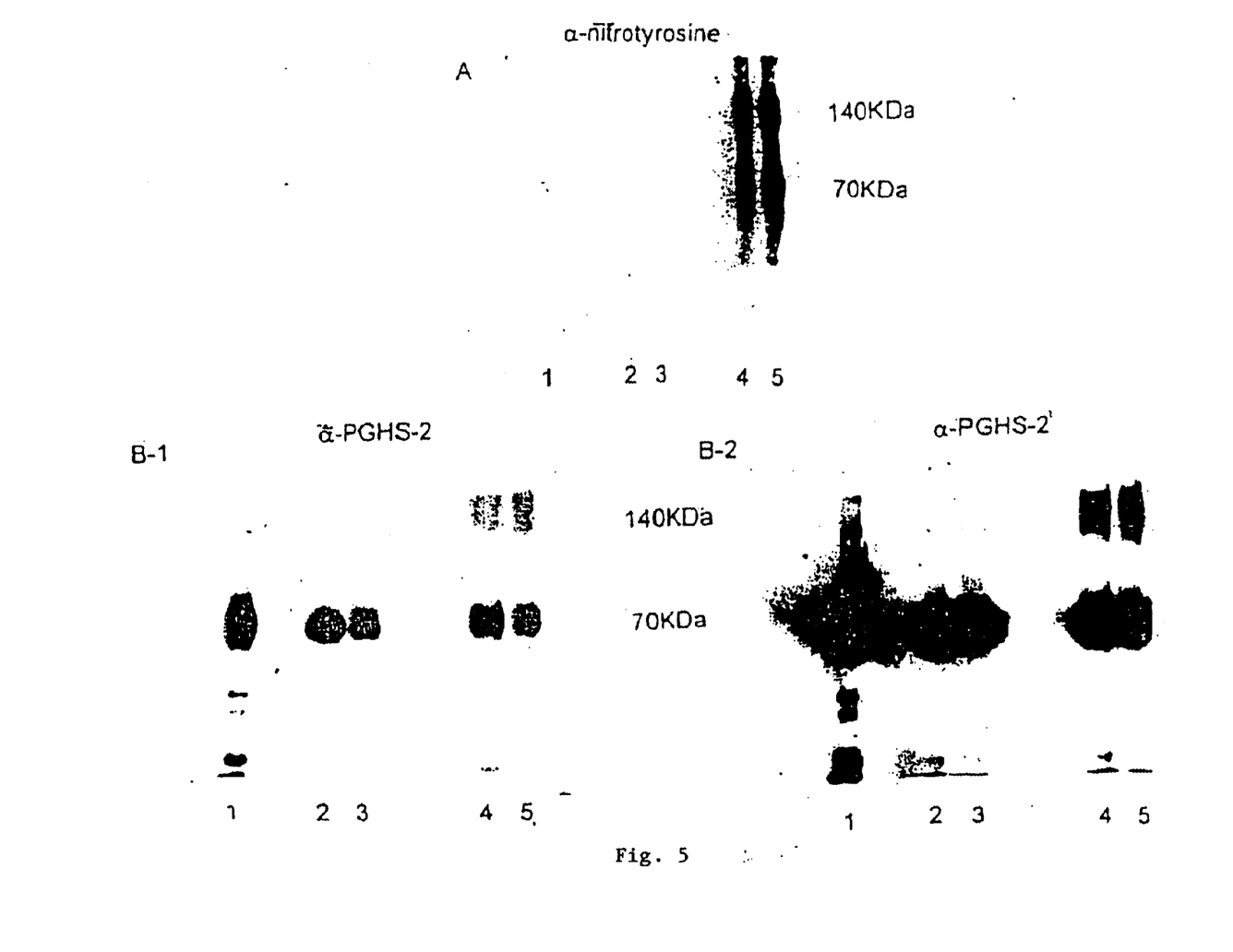

The present experiments also demonstrated that nitration and dimerization of prostaglandin $H_2$ synthase was prevented by the addition of a reducing agent such as GSH (FIGS. 3,5,6). The sulfur hydryl group of GSH quenched activity of toxic oxidants such as peroxynitrite and prevented nitration and dimerization of prostaglandin $H_2$ synthase. It has been reported that peroxynitrite nitrated amino acid residues of proteins (15,17,18). Thus, it was hypothesized that GSH would be nitrated and form a nitrated form of glutathione, GS-NO. However, when the reaction mixture was analyzed by HPLC and the peaks were identified using authentic standards, it was found that no GS-NO was formed. Instead GSH was oxidized to GS-SG, which is a dimerized form of glutathione. This reaction can therefore be utilized to measure the oxidizing power of oxidizing molecules, such as peroxynitrite by measuring the amount of GS-SG formed from GSH. Additionally, a method for using the s-dimerized form of chemical can also include using the formation of an s-dimerized chemical to assess the quenching power of reducing agents, such as antioxidants, against the oxidizing power of molecules, such as peroxynitrite.

The results of the experiment also demonstrated that nitration and polymerization of cytochrome c and prostaglandin $H_2$ synthase by non-disulfide and disulfide bonds, respectively, occurred in vivo and in vitro and that quenching of the nitration and polymerization by addition of GSH were unexpected.

Polymerization can be assessed by visualization of proteins separated by differences in the molecular mass of the polymerized proteins. Separation of polymerized proteins from their monomer can be achieved by SDS-gel or gel filtration chromatography. Nitration can be assessed by Western blot analysis using antibodies against nitrated amino acid residues or by GC/MS of the nitrated amino acid residues.

In general, the assessment of the sample is done utilizing sodium dodecyl sulfate-polyacrylamide gel electrophoresis (SDS-PAGE) with Western blot analysis as described in the Examples set forth herein. However, alternative electrophoresis, such as electrophoresis with Western blot analysis or chromatography can be used. Most of the techniques used in performing SDS-PAGE followed by Western blot analysis are widely practiced in the art, and most practitioners are familiar with the standard resource materials which describe specific conditions and procedures as set forth below.

In general, sample treatment with gel loading buffer with or without β-mercaptoethanol and SDS-PAGE followed by Western blot analysis is employed to assess the status of polymerization and/or nitration of proteins in a specimen. SDS-PAGE followed by Western blot analysis is well known to those skilled in the art.

Available assays that separate polymers from monomers are extensively described in the patent and scientific literature, which can be adapted to be used with the methods of the present invention.

The polymerized cytochrome c and prostaglandin $H_2$ synthase are measured utilizing the SDS-PAGE followed by Western blot analysis, with Coomassie blue stained gel and with antibodies which recognized nitrated tyrosine, cytochrome c and prostaglandin $H_2$ synthase.

The present invention also provides a marker and kit for use in determining oxidant stress. The marker is preferably a polymerized protein. Alternatively, the marker can be a nitrated polymerized protein. In an embodiment, the marker is selected from the group of polymerized prostaglandin $H_2$ synthase, nitrated-polymerized prostaglandin $H_2$ synthase, polymerized cytochrome c, nitrated, polymerized cytochrome c, 30 kDa cytochrome c, nitrated 30 kDa cytochrome c, 45 kDa cytochrome c, and nitrated 45 kDa cytchrome c. Alternatively, the marker can be a disulfide bonded polymerized protein or nitrated disulfide bonded polymerized protein. In these embodiments, the markers are preferably selected from the group consisting essentially of disulfide bonded polymers of prostaglandin $H_2$ synthase and nitrated, disulfide bonded polymers of prostaglandin $H_2$ synthase.

As stated above, the marker can be used in conjunction with a kit for assessing oxidant stress. The kit includes an assay for detecting the polymerized proteins or the nitrated polymerized proteins. The assay can be any of the assays listed above or as any other assays which are known to those of skill in the art to be useful in the kit. The assay requires a detecting device for detecting either the polymerized proteins, nitrated polymerized proteins, the formation of disulfide bonded polymerized proteins, or the formation of nitrated disulfide bonded polymerized proteins.

Further, the present invention provides a method for lowering oxidant stress by adding an effective amount of a reducing agent. A reducing agent prevents the polymerization, nitration or formation of disulfide bonded prostaglandin $H_2$ synthase dimers. This reducing agent, or antioxidant, can be any reducing agent known to those of skill in the art to have the capability of preventing the polymerization of proteins. In the preferred embodiment, the reducing agent is glutathione. However, this is not meant to be limiting but is instead included herein as an example of one reducing agent which is able to use in conjunction with the methods of the present invention. Other examples of reducing agents include glutathione monoethyl ester (GSH precursor), cysteine, methionine and sulfur containing chemicals.

Also provided by the present invention is a pharmaceutical composition for use in lowering oxidant stress. The pharmaceutical includes at least one reducing agent and a pharmaceutically acceptable carrier. The reducing agent, or antioxidant, can be any reducing agent which is able to prevent the polymerization of proteins, nitration of proteins or the nitrated disulfide prostaglandin $H_2$ synthase dimers formation. In the preferred embodiment the reducing agent is glutathione. However, as set forth above, the inclusion of glutathione is intended only for illustrative purposes and not as a limitation. Accordingly, any other reducing agents which are capable of performing in the above indicated manner can also be used without departing from the spirit of the present invention.

The above discussion provides a factual basis for the method of the present invention to measure nitrated and/or polymerized proteins as an assessment of oxidant stress in vitro and in vivo. The methods used with and the utility of the present invention can be shown by the following non-limiting examples and accompanying figures.

EXAMPLES

Materials and Methods

Materials

Sheep prostaglandin $H_2$ synthases form 1 and 2, DETA NONOate (NO donor) and antibodies against nitrotyrosine and prostaglandin $H_2$ synthase were obtained from Cayman Co. (Ann Arbor, Mich.). Goat anti-rabbit immunoglobulin G (IgG) and horseradish peroxidase- and alkaline phosphatase-conjugated donkey anti-rabbit IgG were purchased from Jakson ImmunoResearch Laboratories, Inc. (West Grove, Pa.). Arachidonic acid was obtained from Biomol Research Lab (Plymouth Meeting, Pa.). [$^{14}$C] arachidonic acid was obtained from NEN Life Science Products, Inc. (Boston, Mass.) (specific activity 53 mCi/mmol). Calorimetric substrates of alkaline phosphatase were obtained from BioRad Laboratories (Hercules, Calif.). Electrochemiluminescent substrates of horseradish peroxidase and alkaline phosphatase were obtained from BioRad Laboratories and Amersham Pharmacia Biotech (Piscataway, N.J.), respectively.

Other reagents were obtained from Sigma Chemical Co.

Sodium Dodecyl Sulfate-polyacrylamide Gel Electrophoresis (SDS-PAGE) and Western Blot Analysis SDS-PAGE was carried out on 10% or 15% gels, according to Laemmli (18), with or without the addition of β-mercaptoethanol in gel loading buffer before heat denaturization of proteins. The separated proteins were electroblotted onto a cellulose membrane and Western blot analyses were carried out using alkaline phosphatase system as previously described (19,20). Visualization of bands was accomplished by incubation with a mixture of 5-bromo-4-chloro-3-indolylphosphatate p-toluidine and nitrobluetetrazolium. Western blot analyses were also carried out using horseradish peroxidase or alkaline phosphatase system with electrochemiluminescent substrates.

Prostaglandin $H_2$ Synthase Activity Analysis Using Thin Layer Chromatography (TLC)

Prostaglandin $H_2$ synthase activity analysis of sheep prostaglandin $H_2$ synthases form 1 and 2 obtained from ram seminal vesicle and placenta, respectively, were carried out as previously described (21) with or without pretreatment with peroxynitrite. Briefly, purified or partly purified sheep prostaglandin $H_2$ synthases form 1 (9 units) and form 2 (12 units) were pretreated with or without peroxynitrite at 37° C. for 30 minutes. [$^{14}$C]arachidonic acid (AA) (25 $\mu$M) (NEN, specific activity 53 mCi/mmol) was added to the prostaglandin $H_2$ synthase form 1 or form 2 in 0.2 ml of PBS, and incubated at 37° C. for 10 minutes. Prostaglandin $H_2$ synthase metabolites in the medium were extracted with ethyl acetate, dried down in a centrifugal evaporator, spotted on a silica TLC plate and separated using A-9 solvent (ethyl acetate:trimethylpentane:acetic acid:water, 55:25:10:50). The TLC assay measured products resulting from both the cyclooxygenase and peroxidase activities of prostaglandin $H_2$ synthase. The immediate product of the prostaglandin $H_2$ synthase reaction, prostaglandin $H_2$, was unstable and broke down in a non-enzymatic fashion to a variety of prostaglandins which were detectable by TLC. The Rf pattern in the A-9 solvent system of the break down products of prostaglandin $H_2$ produced by ram seminal vesicle prostaglandin $H_2$ synthase form 1 was well characterized. Thus, prostaglandin $E_2$, prostaglandin $D_2$ and prostaglandin $F_2\alpha$ formed by prostaglandin $H_2$ synthase form 2 were identified by comparing these metabolites with metabolites formed by sheep prostaglandin $H_2$ synthase form 1.

Delivery of Gene Products/therapeutics (Compound)

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound or as pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than the mice or other experimental animals exemplified herein which treatment has a length proportional to the length of the disease process and drug effectiveness. The doses may be single doses or multiple doses over a period of several days, but single doses are preferred.

The doses may be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compound utilized in the present invention can be administered orally to the patient. Conventional methods such as administering the compounds in tablets, suspensions, solutions, emulsions, capsules, powders, syrups and the like are usable. Known techniques which deliver it orally or intravenously and retain the biological activity are preferred.

In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used. The quantity to be administered will vary for the patient being treated and will vary from about 100 ng/kg of body weight to 100 mg/kg of body weight per day and preferably will be from 10 mg/kg to 10 mg/kg per day.

Example 1
Nitrated, Polymerized Cytochrome

Cytochrome c (40 µg) was incubated with 0.5 mM (FIG. 1, Panel A, lane 1) of deactivated (a negative control, FIG. 1, Panel A, lane 2) peroxynitrite in 100 mM phosphate buffer, pH 7.4. Deactivated peroxynitrite was produced by incubation of 0.5 mM peroxynitrite in buffer for 5 minutes prior to addition to the reaction mixture.

After reaction with peroxynitrite or deactivated peroxynitrite, 2 µg of the cytochrome c was separated by SDS-PAGE and electroblotted to a cellulose membrane. Western blot analysis of the electroblotted proteins was carried out with polyclonal antibodies produced against nitrotyrosine using the alkaline phosphatase system. Cytochrome c (14 kDa) treated with peroxynitrite was nitrated and polymerized to 30 kDa, 45 kDa and higher molecular mass (MM) whereas cytochrome c treated with deactivated peroxynitrite failed to be nitrated (FIG. 1, Panel A). The polymerized cytochrome c showed molecular masses of 30 kDa, 45 kDa and a higher molecular mass.

Cytochrome c (40 µg) was incubated with increasing concentrations (0.032 to 0.13 mM) (FIG. 1, Panel B) of peroxynitrite in 100 mM phosphate buffer, pH 7.4. Cytochrome c (0.5 µg) was separated by SDS-PAGE and electroblotted to a cellulose membrane. Western blot analysis of the electroblotted proteins was carried out with polyclonal antibodies produced against nitrotyrosine using the alkaline phosphatase system (FIG. 1, Panel B). The cytochrome c monomer band (14 kDa) shown in Western blot analysis in FIG. 1, Panel B and those obtained from two other experiments were quantitated using Molecular Dynamics Personal Densitometer (FIG. 1, Panel C). This result demonstrates that cytochrome c treated with peroxynitrite was nitrated and polymerized in a dose-dependent manner.

Peroxynitrite-treated cytochrome c and tetranitromethane-treated bovine serum albumin (BSA) were separated by 15% SDS-PAGE and analyzed by Western blot analysis using anti-nitrotyrosine IgG (FIG. 1, Panel D). The tetranitromethane-treated BSA was prepared as previously described (22). The amount of nitrotyrosine per pmol of cytochrome c at each of the peroxynitrite concentrations was calculated on the basis of the nitrated BSA standard curve following quantitation of cytochrome c band (14 kDa) using a Molecular Dynamics Personal Densitometer (FIG. 1, Panal E).

The amino acid composition of cytochrome c analyzed by HPLC after acid hydrolysis revealed that cytochrome c contained tyrosine residues. Peroxynitrite treatment of the cytochrome c decreased the tyrosine peak in a chromatogram of the HPLC. Both cysteine residues in cytochrome c are not available for nitration because they are covalently bound to the heme prosthetic group. Thus, nitration of cytochrome c with peroxynitrite results in nitration of tyrosine residues but not cysteine residues.

Example 2
Nitrated Cytochrome C (14 kDa), 30 kDa Species and 45 kDa Species Produced by Oxidant Stress Mediated by Prostaglandin $H_2$ Synthase Cytochrome c was nitrated and polymerized by peroxynitrite treatment (FIG. 1) as discussed in EXAMPLE 1.

Reaction mixture in 100 mM phosphate buffer, pH 7.4, (total volume, 200 µl) was incubated at 37° C. for 30 minutes. The reaction mixture contained a combination of cytochrome c (40 µg), ovine prostaglandin $H_2$ synthase form 2 (104 units), arachidonic acid (590 µM), epinephrine (31 µg), hematin (1 µM), and DETA NONOate, an NO donor, (300 µM) as indicated in FIG. 2. After incubation, the proteins were separated by SDS-PAGE followed by Western blot analysis with an alkaline phosphatase system using monoclonal antibodies produced against nitrotyrosine.

By this experiment, it was found that cytochrome c could be nitrated and polymerized when peroxynitrite was replaced with a NO donor (DETA NONOate) in presence of prostaglandin $H_2$ synthase in an arachidonic acid-dependent manner (FIG. 2). This result suggested that nitration of cytochrome c, the 30 kDa species and 45 kDa species, was a result of transformation of NO to a reactive molecule, e.g. peroxynitrite, during prostaglandin $H_2$ synthase-dependent metabolism of arachidonic acid. Triplet bands of prostaglandin $H_2$ synthase form 2 in Western blot analysis were a result of the specific interaction of nitrotyrosine residues of prostaglandin $H_2$ synthase with antibodies against nitrotyrosine.

Figure 4:
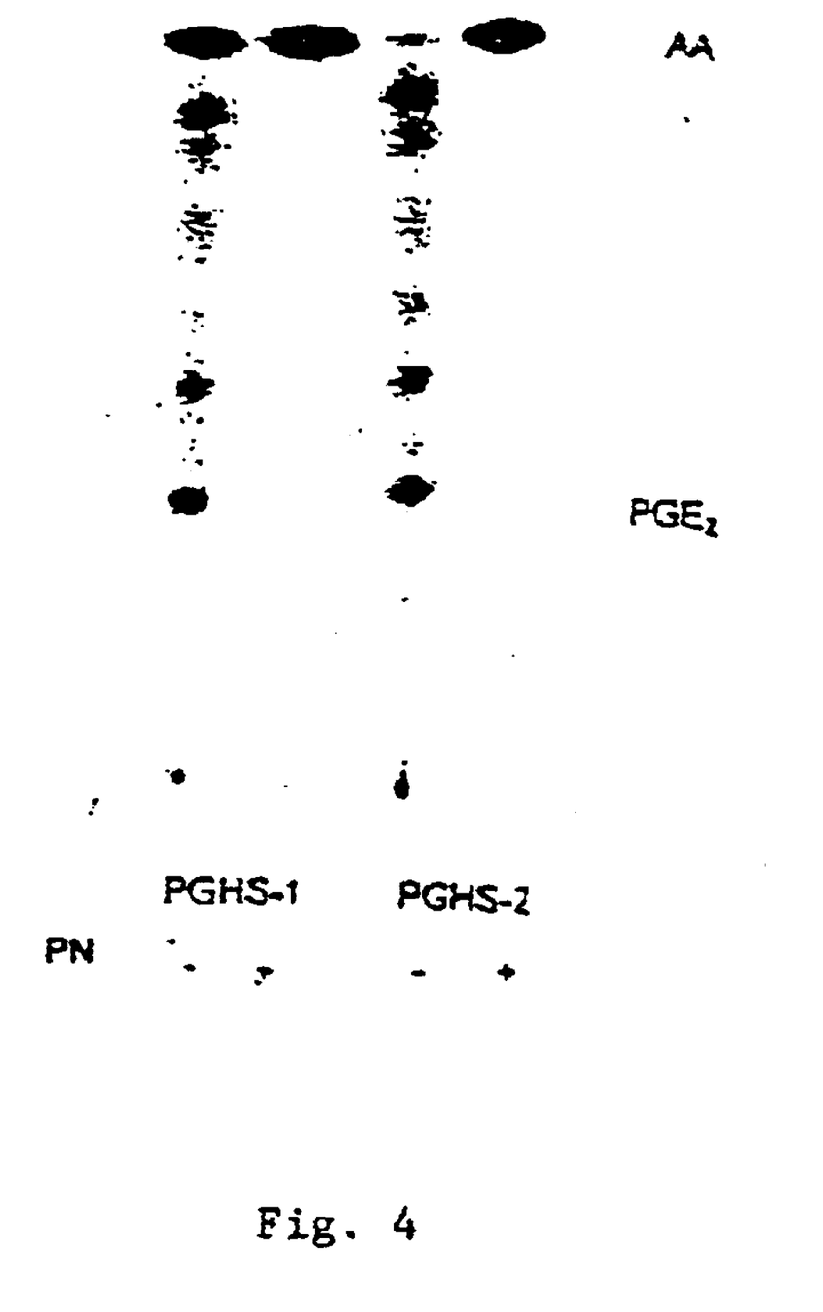
FIG. 4 shows the effect on catalytic activities of prostaglandin $H_2$ synthases form 1 (PGHS-2) and form 2 (PGHS-2) after incubation with peroxynitrite (PN); either sheep PGHS-2 or PGHS-2 was treated with PN prior to measuring the metabolic activity of the enzymes; activity was determined by conversion of $^{14}C$-arachidonic acid (AA) to its metabolites and visualized by thin layer chromatography (TLC)

Example 3
Nitrated and Polymerized Prostaglandin $H_2$ Synthase Produced in Vitro and in Vivo and Inhibition of Nitration and Polymerization by Addition of a Reducing Agent Treatment of prostaglandin $H_2$ synthase form 2 with peroxynitrite increased nitration of tyrosine residues (FIG. 3, Panel A, lanes 4 and 5). Contrary to the previously reported results that nitration of a cysteine residue of ovine prostaglandin $H_2$ synthase form 1 enhanced catalytic activity by alteration of secondary structure of the enzyme (13), nitration induced by peroxynitrite treatment abolished the catalytic activities of both prostaglandin synthases form 1 and 2 (FIG. 4).

Addition of glutathione (GSH) inhibited the nitration of tyrosine residues of prostaglandin $H_2$ synthase form 2 (FIG. 3, Panel A, lanes 2 and 3). HPLC analysis of the reaction mixture containing GSH after peroxynitrite treatment revealed a decrease in the GSH level and a concurrent increase in the oxidized glutathione (GS-SG) level in addition to the appearance of an unidentified peak. Nitrated glutathione which was predicted to be formed after peroxynitrate treatement, nitrosoglutathione (GS-NO), (see FIG. 3, Panel B) was ruled out as a possible candidate for the unidentified product based on HPLC analysis.

Whether prostaglandin $H_2$ synthase was dimerized after peroxynitrite treatment via a cysteine-disulfide bond was determined using SDS-PAGE without addition of β-mercaptoethanol (βME) in the gel loading buffer (FIG. 5, Panels A and B-2 and B-2, lanes 4 and 5). The peroxynitrite-treated samples migrated both as a monomer (70 kDa) and a dimer (140 kDa). This experiment revealed that prostaglandin $H_2$ synthase form 2 was dimerized via a disulfide bond.

Prostaglandin $H_2$ synthase form 2 samples treated with peroxynitrite in the presence of GSH ran as a monomer (FIG. 5, Panels B-2 and B-2, lanes 2 and 3) which was not nitrated (FIG. 5, Panel A, lanes 2 and 3). These results clearly demonstrated that peroxynitrite treatment of prostaglandin $H_2$ synthase produced nitrotyrosine and induced dimerization of PGHS-2 and formation of nitrotyrosine and dimerization of prostaglandin $H_2$ synthase were blocked by GSH.

Sheep placenta prostaglandin $H_2$ synthase form 2 contained nitrated tyrosine as evidenced by the Western blot analysis with antibodies against nitrotyrosine (FIG. 6, Panel A). Immunoreactivity of the anti-tyrosine antibodies with the sheep placenta prostaglandin $H_2$ synthase form 2 dramatically decreased after incubation with the primary antibody solution containing nitrotyrosine. This result shows that indeed the native prostaglandin $H_2$ synthase form 2 contained nitrotyrosine formed in vivo.

Levels of nitrotyrosine in native proteins reflect in vivo oxidant stress. In addition, the native sheep prostaglandin $H_2$ synthase was found dimerized via a disulfide bond (FIG. 6, Panel B-3). In the presence of βME, native sheep placenta prostaglandin $H_2$ synthase form 2 was a monomer whereas in the absence of βME, the prostaglandin $H_2$ synthase form 2 was a mixture of a monomer and a dimer (FIG. 6, Panel B-2 and B-2). Only the dimeric form of the prostaglandin $H_2$ synthase form 2 was nitrated (FIG. 6, Panel B-3). These results show that the dimeric form of prostaglandin $H_2$ synthase form 2 was formed via a disulfide bond in vivo and only the dimeric form was nitrated.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the described invention, the invention may be practiced otherwise than as specifically described.

REFERENCES

1. Smith, W. L. Marnett, L. J. Biochim. Biophys. Acta, 1083: 1–17(1991).
2. Baker, R. R. Clin. Biochem., 23: 455–458(1990).
3. Smith, W. L. Biochem. J., 259: 315–324(1988)
4. Lote, C. J. Haylor, J. Portages. Leukos. Essen. Fatty Acids, 36: 203–217 (1989).
5. Xei, W., Robertson, D. L. and Simmons, D. L. Drug. Develop. Res. 25:249–265 (1992).
6. Kujubu, D., Fletcher, B., Varnum, B., Lim, R., & Hershman, H. R. J. Biol. Chem. 266:12866–12872 (1991).
7. Smith, W. L. and DeWitt, D. L. Advances in Immunol. 62: 167–215 (1996)
8. White, S. Prostagland. Leuk. Essent. Fatty, 43: 209–222 (1991).
9. Miller, M. J. S., Thompson, J. H., Zhang, X-J., Sadowskakrowicka, H., Kakkis, J. L., Munshi, U. K., Sandoval, M., Rossi, J. L., Elobychildress, S., Beckman, J. S., Ye, Y. Z., Rodi, C. P., Manning, P. T., Currie, M. G., and Clark, D. A. (1995) Gastroenterology 109, 1475–1483.
10. Reuter, B. K., Asfaha, S., Buret, A., Sharkey, K. A., and Wallace, J. L. (1996) J. Clin. Invest., 98, 2076–2085.
11. Singer, I. I., Kawka, D. W., Scott, S., Weinder, J. R., Mumford, R. A., Riehl, T. E., and Stenson, W. F. (1996) Gastroenterology 111, 871–885.
12. Green, D. R. and Reed, J. C. (1998) Science 281, 1309–1312 and references therein.
13. Gunther, M. R., Hsi, L. C., Curtis, J. F., Gierse, J. K., Marnett, L. J., Eiling, T. E., and Mason, R. P. (1997) J. Biol. Chem. 272, 17086–17090.
14. Rossig, L., Fichtlscherer, B., Breitschopf, K., Haendeler, J., Zeiher, A. M., Mulsch, A., and Dimmeier, S. (1999) J. Biol. Chem. 274, 6828–6826.
15. Lepoivre, M., Fieschi, F., Coves, J., Thelander, L., Fontecave, M. (1991) Biochem. Biophys. Res. Commun. 179, 442–448.
16. Roberts, E. S., Lin, H-L., Crowley, J. R., Vuletich, J. L., Osawa, Y., and Hollenberg, P. F. (1998) Chem. Res. Toxicol. 11, 1067–1074.
17. Hajjar, D. P., Lander, H. M., Pearce, S. F. A., Upmacis, R. K., and Pomerantz, K. B. (1985) J. Am. Chem. Soc. 117, 3340–3346.
18. Laemmli, U. K. (1970) Nature, 277, 680–685.
19. Kim, H., Kim, S. G., Lee, M. Y., and Novak, R. F. (1992) Biochem. Biophys. Res. Commun. 186, 846–853.
20. Kim, H., Putt, D., Reddy, S., Hollenberg, P. F., and Novak, R. F. (1993) J. Pharmacol. Exp. Ther. 267, 927–936.
21. Hla, T., and Neilson, K., Proc. Natl. Acad. Sci. U.S.A. 89:7384–7388(1992).
22. Ye, Y. Z., Strong, M., Huang, Z. and Beckman, J. S. (1996) in Methods in Enzymology (Packer, L. ed) vol. 269, pp. 201–209, Acedemic Press Inc., New York, N.Y.

What is claimed is:

1. A method of assessing levels of oxidant stress by measuring non-aggregated, covalent bond-polymerized proteins formed after mixing oxidants with proteins and non-aggregated, covalent bond-polymerized proteins of biological specimens comprising the steps of:

separating non-aggregated proteins from aggregated proteins by difference in solubility of the proteins in buffer solution;

separating non-aggregated proteins by differences in the molecular mass using sodium dodecyl sulfate-polyacrylamide gel electrophoresis (SDS-PAGE) or chromatography under denaturing condition of a purified and mixtures of proteins;

visualizing proteins with protein staining and Western blot analysis using antibody against the proteins, respectively; and measuring increased levels of polymerized protein as an indication of increased levels of oxidative stress.

2. The method according to claim 1, wherein said measuring step further comprises measuring nitrated, polymerized proteins.

3. The method according to claim 2, wherein said measuring step includes measuring polymerized proteins selected from the group consisting of polymerized cytochrome c, nitrated-polymerized cytochrome c, 30 kDa cytochrome c, nitrated 30 kDa cytochrome c, 45 kDa cytochrome c, and nitrated 45 kDa cytochrome c.

4. A kit for use in assessing oxidant stress by measuring non-aggregated, covalent bond-polymerized proteins formed after mixing oxidants with proteins and non-aggregated, covalent bond-polymerized proteins of biological specimens comprising the steps of separating non-aggregated proteins from aggregated proteins by differences in solubility of the proteins in buffer solution;

separating non-aggregated proteins by differences in the molecular mass using sodium dodecyl sulfate-polyacrylamide gel electrophoresis (SDS-PAGE) or chromatography under denaturing condition of a purified and mixtures of proteins;

visualizing proteins with protein staining and Western blot analysis using antibody against the proteins; and measuring increased levels of polymerized protein as an indication of increased levels of oxidative stress.

5. The kit according to claim 4, wherein said assay further includes means for detecting nitrated polymerized proteins.

6. The kit according to claim 4, wherein said assay further includes means for detecting the formation of disulfide bonded polymerized proteins.

7. The kit according to claim 4, wherein said assay further includes means for detecting the formation of nitrated disulfide bonded polymerized proteins.

8. A method of assessing levels of oxidant stress by measuring non-aggregated, disulfide polymerized proteins formed after mixing oxidants with proteins and non-aggregated, disulfide polymerized proteins of biological specimens comprising the steps of:

only measuring levels of a non-aggregated, disulfide polymerized proteins by separating non-aggregated proteins from aggregated proteins by differences in solubility of the proteins in buffer solution;

separating non-aggregated proteins by differences in the molecular mass using sodium dodecyl sulfate-polyacrylamide gel electrophoresis (SDA-PAGE) or chromatography under denaturing condition of a purified and mixtures of proteins without breaking disulfide bond of polymers;

visualizing proteins with protein staining and Western blot analysis using antibody against the proteins, respectively, and measuring a level of a non-aggregated, disulfide polymerized proteins from the same sample by breaking disulfide bond of polymers by the addition of a chemical; and measuring increased levels of disulfide bonded, polymerized protein by comparing results obtained with and without breaking bonds of the protein as an indication of increased levels of oxidative stress.

9. The method according to claim 8, wherein said measuring step includes measuring the formation of nitrated-disulfide polymerized proteins.

* * * * *